US006932914B2

(12) United States Patent
LeClair

(10) Patent No.: US 6,932,914 B2
(45) Date of Patent: Aug. 23, 2005

(54) METHOD AND APPARATUS FOR THE CONTROLLED FORMATION OF CAVITATION BUBBLES USING TARGET BUBBLES

(76) Inventor: Mark L. LeClair, 25 Jesse Daniel Dr., Buxton, ME (US) 04093

( * ) Notice: Subject to any disclaimer, the term of this patent is extended or adjusted under 35 U.S.C. 154(b) by 493 days.

(21) Appl. No.: 10/263,067

(22) Filed: Oct. 1, 2002

(65) Prior Publication Data

US 2003/0136756 A1 Jul. 24, 2003

Related U.S. Application Data

(60) Provisional application No. 60/350,849, filed on Jan. 18, 2002.

(51) Int. Cl.[7] .................................................. B44C 1/22
(52) U.S. Cl. ............................ 216/52; 216/56; 216/83; 216/94; 219/121.2; 219/121.43; 219/121.69; 606/2
(58) Field of Search .............................. 216/52, 56, 83, 216/85, 92, 94; 606/2, 9; 128/898; 156/345; 219/121.12, 121.18, 121.36, 121.39, 121.4, 121.43, 121.6, 121.69

(56) References Cited

U.S. PATENT DOCUMENTS

| 5,057,184 A | * | 10/1991 | Gupta et al. ................. 216/65 |
| 6,135,998 A | * | 10/2000 | Palanker ...................... 606/39 |
| 6,547,779 B2 | * | 4/2003 | Levine et al. .................. 606/7 |
| 2002/0045911 A1 | * | 4/2002 | Fletcher et al. ............. 606/167 |
| 2003/0139041 A1 | * | 7/2003 | LeClair ....................... 438/689 |
| 2004/0004055 A1 | * | 1/2004 | Barros .......................... 216/13 |
| 2004/0054357 A1 | * | 3/2004 | O'Donnell ..................... 606/4 |
| 2005/0064137 A1 | * | 3/2005 | Hunt et al. .................. 428/131 |

FOREIGN PATENT DOCUMENTS

WO   WO 2003/061921 A2 * 7/2003 ............. B26F/3/00

OTHER PUBLICATIONS

Akhatov et al. "Collapse and rebound of a laser–induced cavtation bubble" Physics of Fluids, vol. 13, No. 10, pp. 2805–2819 Oct., 2001.*
Song et al "Laser–induced cavtation bubbles for cleaning of solid su/aces" Journal of Applied Physics, pp 2952–2956. Mar. 15, 2004*, vol. 95, No. 6.*
Gaze et al. "Laser Generated Cavitation Near a Curved Surface", Lasers and Electro–optics Europe, 2000 Conference Digest. 2000 Conference on, Sep. 10–15, 2000. pp. 1.*
Blake et al, Boundary Integral Methods for Cavitation Bubbles Near Boundaries, CAV2001: Fourth International Symposium on Cavitation, California Institute of Teehnology, Jun. 20–23, 2001.*

* cited by examiner

Primary Examiner—A. Farah
(74) Attorney, Agent, or Firm—D'Arcy H. Lorimer; Claude A. S. Hamrick

(57) ABSTRACT

The present invention discloses a method and apparatus for the directed formation of a re-entrant micro-jet formed upon the collapse of a working cavitation bubble formed proximate to a work surface. A target bubble, formed between the work surface and the working cavitation bubble, is utilized to direct the re-entrant micro-jet to the work surface.

21 Claims, 15 Drawing Sheets

Fig. 3a 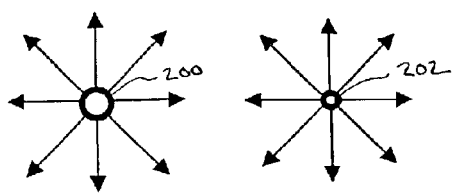 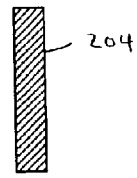
Fig. 3b 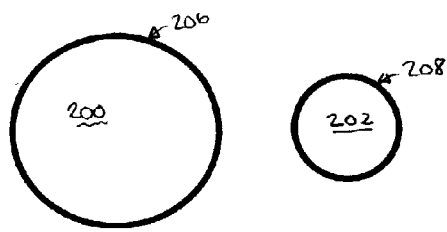 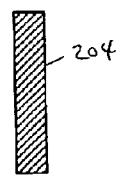
Fig. 3c 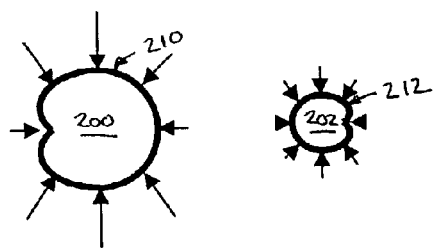 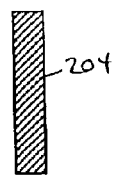
Fig. 3d 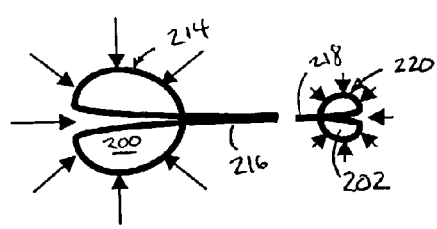 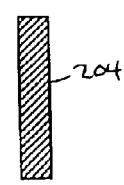

Fig. 4a 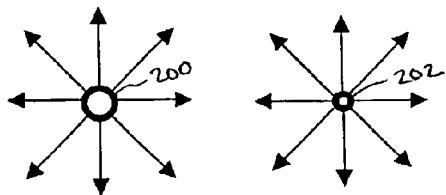 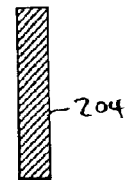
Fig. 4b 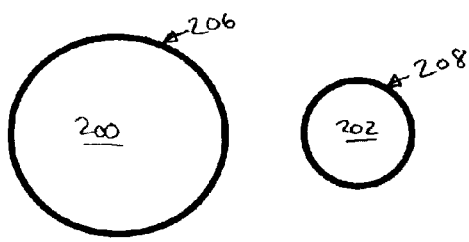 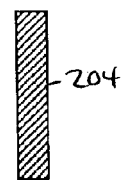
Fig. 4c 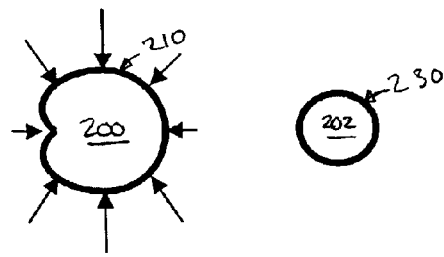 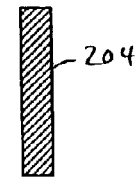
Fig. 4d 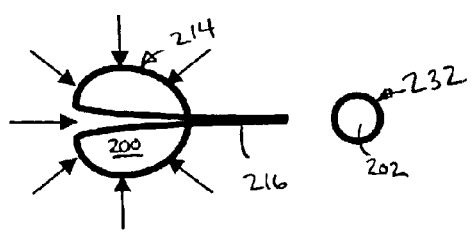 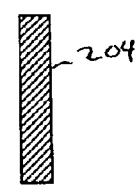

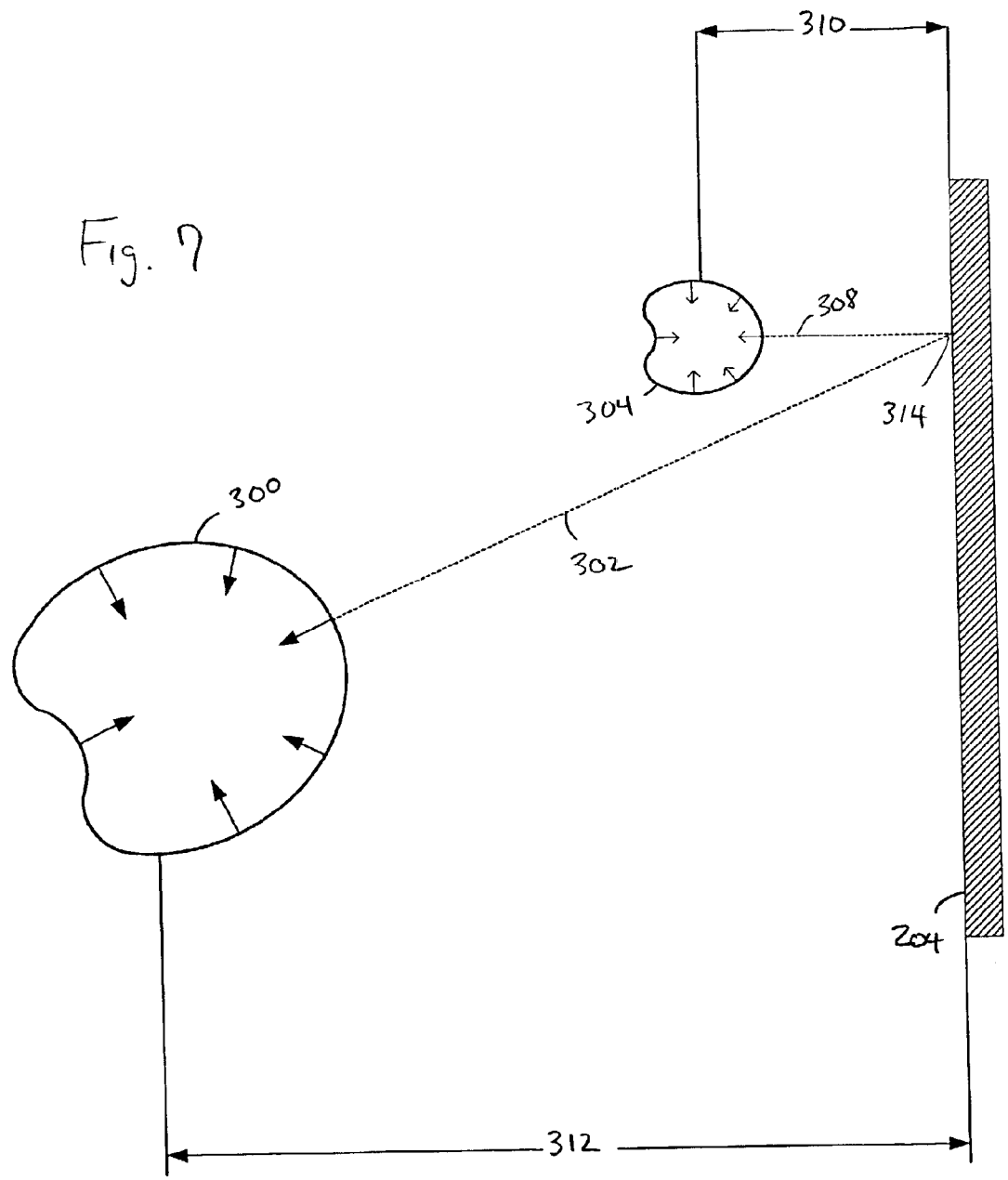

METHOD AND APPARATUS FOR THE CONTROLLED FORMATION OF CAVITATION BUBBLES USING TARGET BUBBLES

CROSS REFERENCE TO RELATED APPLICATIONS

This application is related to provisional application No. 60/350,849 filed Jan. 18, 2002 entitled METHOD AND APPARATUS FOR THE CONTROLLED FORMATION OF CAVITATION BUBBLES, claims benefit thereof, and is incorporated entirely herein by reference.

BACKGROUND OF THE INVENTION

1. Field of the Invention

This invention relates generally to the formation and control of individual micron size and submicron size cavitation bubbles for use in nanofabrication operations. More particularly, embodiments of the invention teach methods and apparatus for control of a re-entrant micro-jet formed upon collapse of an individual or array of cavitation bubbles and directing the impact of the micro-jet toward a work surface or other objects with a high degree of precision.

2. Description of the Related Art

In general, the production of cavitation has been a phenomena many have tried to avoid. Cavitation in a liquid is the formation, growth, and collapse of gaseous and vapor bubbles due to the reduction of pressure below the vapor pressure of the liquid at the working temperature. Pump impellers, boat props, and similar applications experience cavitation which can produce rapid damage and erosion of surfaces. It has been well known for many years that ultrasonic cleaning devices, which function by the creation of cavitation bubbles, can produce significant surface damage to even the hardest of materials. Studies by a number of authors have revealed that one significant element in producing the damage caused by cavitation occurs when a cavitation bubble collapses in the vicinity of a surface, launching what is called a re-entrant micro-jet toward the surface. This liquid jet can produce velocities as high as 1500 m/s, and is capable of damaging the hardest materials known.

Recently, a number of applications have been developed utilizing the formation of cavitation bubbles through the use of laser light or electrical discharge. Esch et al. (U.S. Pat. No. 6,139,543) and Herbert et al. (U.S. Pat. No. 6,210,400) disclose the use of laser light introduced into a catheter device for the purpose of creating cavitation bubbles, whose expansion and collapse are utilized to pump fluids in and out of the catheter. Hammer et al. (U.S. Pat. No. 5,738,676) discloses a laser surgical probe with a special lens designed to produce the cavitation bubbles further from the end of the fiber optics, to reduce the damage formed (presumably by the reentrant micro-jets launching into the lens on the end of the cable). Such damage was also reported by Rol et al. in "Q Switched Pulses and Optical Breakdown Generation Through Optical Fibers", Laser and Light in Ophthalmology, Vol. 3, No. 3, 1990. Palanker (U.S. Pat. No. 6,135,998) describes a method for performing electrosurgery using sub-microsecond, high power electrical pulses applied to an electrosurgical probe interface. The tool described by Palanker provides a cutting force by both the plasma generated by the electrical arc and shock waves produced by collapsing cavitation bubbles.

In each of the prior art references cited above, there has been no attempt to control the direction and impact of the powerful micro-jets formed upon the collapse of the cavitation bubbles created when highly focused energy is introduced into a liquid. Without such control, concern of collateral damage cannot be avoided, especially when such tools are used in the human body in a medical application.

Recently as well, there has been a significant interest generated in the field of nanotechnology, for methods needed to fabricate micron and submicron devices and nanomachines. There are very few fabrication tools available that can cut, drill, peen, deform, or otherwise modify features of a surface on a submicron to nanometer scale. Much of the technology developed by the semiconductor industry requires the fabrication of structures utilizing photolithographic processing. This technology is not as flexible as may be required, and will have certain difficulties when applied to biological nanotechnology systems. Advancing the state of the art required by nanotechnology applications will require fabrication technologies operating at least 1 to 2 orders of magnitude below that capable in the semiconductor process arena.

The invention as described in the above referenced provisional application provides a method for the controlled formation of individual cavitation bubbles comprising immersing a mask including at least one aperture within a liquid, immersing a work piece having a work surface in the liquid proximate to the mask, generating a cavitation bubble proximate to the aperture such that the mask is located between the cavitation bubble and the work piece. A re-entrant micro-jet formed during the collapse of the cavitation bubble is directed through the aperture to the work surface. An apparatus for the controlled formation of cavitation bubbles as described in the above referenced provisional application includes a mask having at least one aperture, immersed in a liquid, and an energy source having an energy flow in the liquid sufficient to create at least one cavitation bubble. The energy flow creates the cavitation bubble proximate to the aperture and the collapse of the cavitation bubble creates a re-entrant micro-jet directed through the aperture to a work surface. While this technique is very useful for processing surfaces that can be located conveniently in the vicinity of a fixed orifice, there are many other situations where one may wish dynamic, three dimensional control of the direction of the re-entrant micro-jet. These situations may include eye surgery, for example, where placing an orifice structure inside the eye may not be practical.

The prior state of the art therefore has yet to provide a fabrication technology capable of operating in the nanometer region by harnessing the powerful phenomena of the re-entrant micro-jet formed during the collapse of a precisely located cavitation bubble. What is further needed is a method and apparatus to precisely control the direction and location of the re-entrant micro jet without the encumbrance of physical structure such an orifice between the work surface and the cavitation bubble.

SUMMARY OF THE INVENTION

The present invention provides a method for the directed formation of a re-entrant micro-jet including immersing a work piece having a work surface in a liquid, generating a working cavitation bubble proximate to the work surface and generating a target bubble between the work surface and the working cavitation bubble, wherein a re-entrant micro-jet formed upon the collapse of the working cavitation bubble is directed to the work surface.

An apparatus for the directed formation of a re-entrant micro-jet in accordance with the present invention includes a vessel containing a liquid within which a work piece having a work surface may be immersed, a first energy source for producing a first energy flow in the liquid sufficient to create a working cavitation bubble proximate to the work surface and a second energy source for producing a second energy flow in the liquid sufficient to create a target cavitation bubble between the work surface and the working cavitation bubble. The re-entrant micro-jet formed upon the collapse of the working cavitation bubble engages the work surface in a direction influenced by the position of the target bubble.

BRIEF DESCRIPTION OF THE DRAWINGS

FIGS. 3a–3e are schematic diagrams showing a sequence for directing a re-entrant micro-jet toward a work surface through a target bubble in close proximity to the working bubble in accordance with the present invention;

FIGS. 4a–4e are schematic diagrams showing a sequence for directing a re-entrant micro-jet toward a work surface through a target bubble far from the working bubble in accordance with the present invention;

FIG. 7 is a schematic diagram of a working bubble and a target bubble directing convergent re-entrant micro-jets to a work surface in accordance with the present invention;

DETAILED DESCRIPTION OF THE PREFERRED EMBODIMENT(S)

Figure 1:
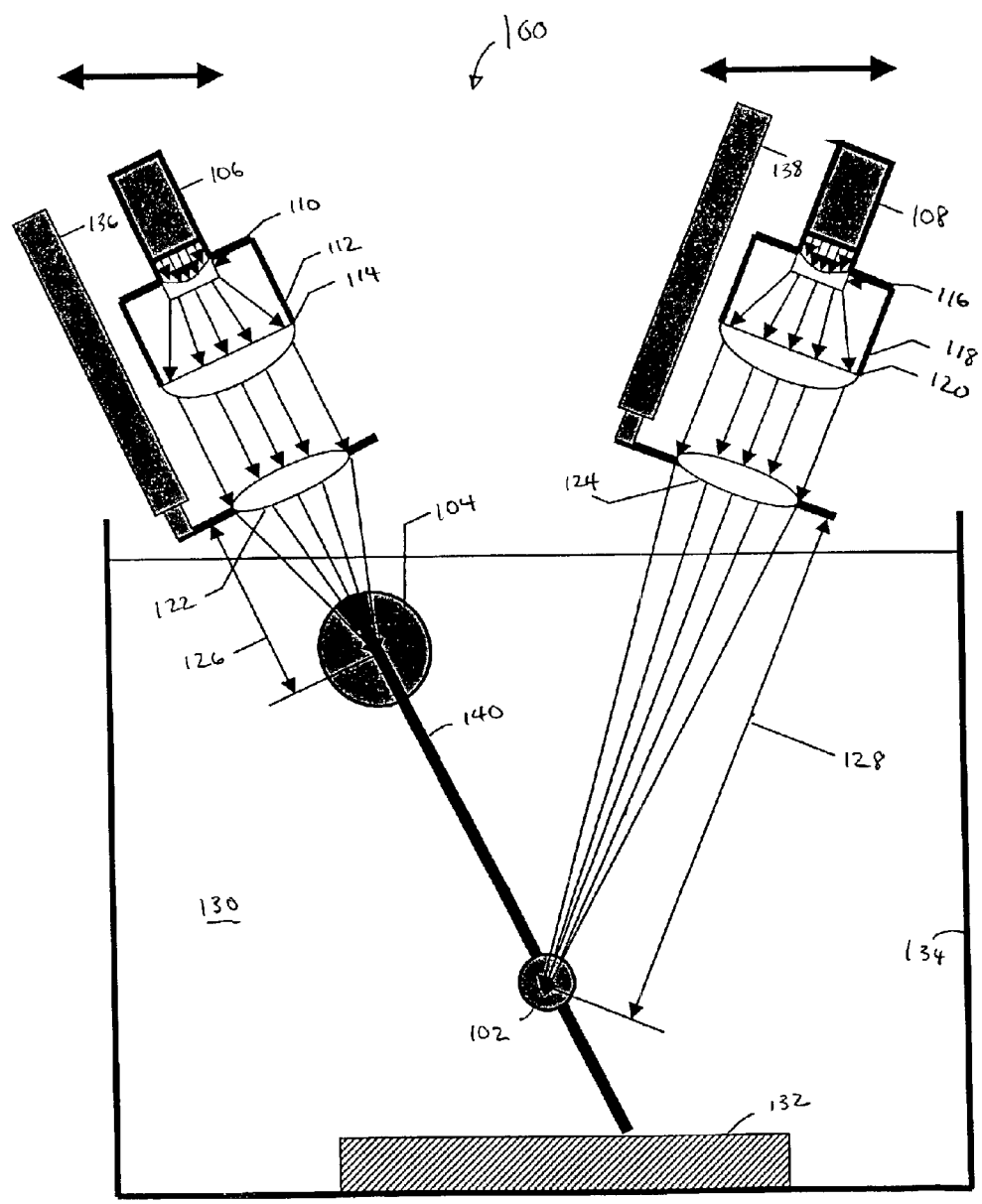
FIG. 1 is a cross sectional view of an apparatus for generating target bubbles and cavitation bubbles in accordance with the present invention.

The control and direction of the re-entrant micro-jet formed during the collapse of a cavitation bubble can provide a powerful tool for performing various fabrication and manipulation functions at a submicron and nanometer scale. The above mentioned provisional U.S. patent application describes how these re-entrant micro-jets may be controlled through the use of an orifice placed between the work surface and the collapsing cavitation bubble. While the aforementioned techniques shall prove very useful for fabrication processes where the work surface can be placed in proximity to an orifice structure, there may be other applications where placing such a structure will be difficult or impossible. One example might be surgery inside the human eye, where a surgeon might wish to generate re-entrant micro-jets in the humus by focussing laser beams through the cornea. Another example might be to cut features into the side wall of micron sized pores in an integrated circuit structure where fabricating and placing submicron orifice structures would be very difficult.

In general, the formation of cavitation bubbles from a focussed energy source can be described as follows. The energy from a cavitation initiation device is focused into a small volume in proximity to a work piece surface. The intense energy focused into the small focus volume is absorbed by the fluid, causing rapid boiling and expansion of vaporized gasses. Energy sources may include, but are not limited to: lasers, x-ray sources, ultrasound, electrical discharge, and positrons.

The cavitation bubble, formed from the rapid expansion of vaporized fluid and the momentum of liquid moving away from the center of the focus volume, reaches a maximum diameter at the end of the expansion process. Typically, the maximum diameter of the fully expanded cavitation bubble is approximately 10 to 50 times the diameter of the focus volume, and is determined by amount of energy absorbed by the fluid in the focus volume. Not all the energy introduced into the focus volume is absorbed by the fluid. The amount actually absorbed depends on the chemical characteristics of the fluid and the coupling efficiency of a particular energy source. Gas pressure inside fully expanded cavitation bubble may be as low as the vapor pressure of the fluid at it's bulk temperature. This is due, in part, to the momentum of the expansion process which does not terminate when the bubble reaches an internal pressure equal to that of the surrounding fluid, but continues until the pressure is reduced to the vapor pressure of the surrounding liquid. The pressure of the surrounding fluid, typically at 1 atmosphere absolute or higher, creates a pressure differential on the outer surface of the cavitation bubble, driving its subsequent collapse. For fluids such as water at 1 atmosphere and 25° C., the pressure differential can exceed 700 torr.

Following the initial collapse of the outer surface of the cavitation bubble, a re-entrant micro-jet is launched toward the work surface. The fully formed re-entrant micro-jet may impact the work surface with velocities as high as 1500 meters/second, and is capable of removing material from the hardest surfaces known, such as diamond. These jets may be used to cut, machine, drill through, erode or deform features on the work surface. The diameter of the jets are determined by the size of the cavitation bubble formed, which in turn is determined by the dimensions of the focus volume and the level of energy introduced into the focus volume. The re-entrant micro-jet diameters may vary from about 1 micron to about 1 nanometer for focused laser and x-ray energy sources. Electric discharge sources may produce re-entrant micro-jet diameters on the order of 10 to 15 microns. The impact force of the re-entrant micro-jet on work surface may be adjusted by altering the distance to the work surface. At a given jet velocity, the impact force will vary inversely with the distance.

The present invention teaches a technique by which the re-entrant micro-jet formed during the collapse of a primary cavitation bubble (hereinafter called the working bubble) can be directed by the creation of a second bubble (hereinafter called the target bubble) within a given proximity of the collapsing working bubble. Target bubbles can be created in any direction in $3d$ space relative to the center of the working bubble. All that is required is that there be a clear line of sight (relative to the radiation source needed to create the bubble) to the projected position of the target bubble; that the target bubble is formed within a given time period of the collapse of the working bubble; and that the target bubble be within a given proximity of the working bubble. The target bubble serves to attract the re-entrant micro-jet by creating a hydrodynamic condition similar to that of a solid work surface or an orifice. However, the target bubbles, unlike solid work surfaces, are transparent to the jets, and allow the jets to slice through them unimpeded. Target bubbles can therefore be used to direct the powerful re-entrant micro-jets toward a work surface or object without the need for an orifice. To be effective, a target bubble should be within approximately 6 maximum working bubble diameters of the working bubble. A maximum working bubble diameter is defined as the maximum diameter obtained by the working bubble just prior to collapse. The maximum working bubble diameter may be predetermined by estimating the energy being delivered to the control volume (i.e. the energy delivered in each pulse of a laser), estimating the adsorption coefficient of the energy within the fluid, computing the amount of fluid vaporized using well known thermodynamic principles, and computing the volume of the gas bubble at a given pressure (approximately the vapor pressure of the liquid at the bulk temperature). The maximum working bubble diameter may also be predetermined by correlation of experimental observations, where the maximum diameters are measured under a variety of conditions and correlated to the input variables such as laser pulse power and fluid parameters.

FIG. 1 is a cross sectional view of an apparatus 100 for generating target bubbles 102 and working (cavitation) bubbles 104 in accordance with the present invention. A work piece 132 is placed in a container 134 filled with fluid 130. Components 108, 116, 118, 120, 124, and 138 make up a focussed laser device for creating the target bubble 102. Components 106, 110, 112, 114, 122, and 136 make up a focussed laser device for creating the cavitation working bubble 104. The lasers 106 and 108 may be chosen from among the group of CO2, Nd-YAG, dye, or excimer types. Other focussed energy devices such as x-ray and electrical discharge electrodes may also be used to create bubbles 104 and 106, as is well known to those skilled in the art. Alternatively, target bubbles 102 may be created by sparging gas though nozzles and orifices, and allowing them to rise through the fluid proximate to the working bubble. Radiation produced by laser 108 is expanded by lens 116 and collimated by lens component 120 and focussed distance 128 by lens 124. Lens 124 is coupled to focussing mechanism 138. Lenses 116 and 120 are held in position by support 118. The intense laser radiation focussed into a small control volume vaporizes the liquid in that volume and creates the cavitation target bubble 102. In like manner, laser 106 and lens components 110, 114, and 122 create the cavitation working bubble 104 at a distance 126. Support 112 and focussing mechanism 136 perform analogous functions to those described above for support 118 and mechanism 138. Re-entrant micro-jet 140 is formed upon the collapse of the working cavitation bubble 104, and is attracted through target bubble 102 to work surface 132. By altering the angular orientation of lasers 106 and 108, and the focal distances 126 and 128, the re-entrant micro-jet can be positioned to impact anywhere on work surface 132. By altering the distance of the working bubble 104 to the work surface 132, the impact force of the jet may also be altered, as described previously. To be effective in directing the re-entrant micro-jet, the target bubble should be within approximately six maximum working bubble diameters of the working bubble. The fluid in tank 134 can be any appropriate fluid that absorbs the laser radiation being utilized, but is preferably water or a solution containing water. The fluid may be re-circulated and filtered by additional pumps and components (not shown) to maintain an appropriate optical clarity.

Figure 2:
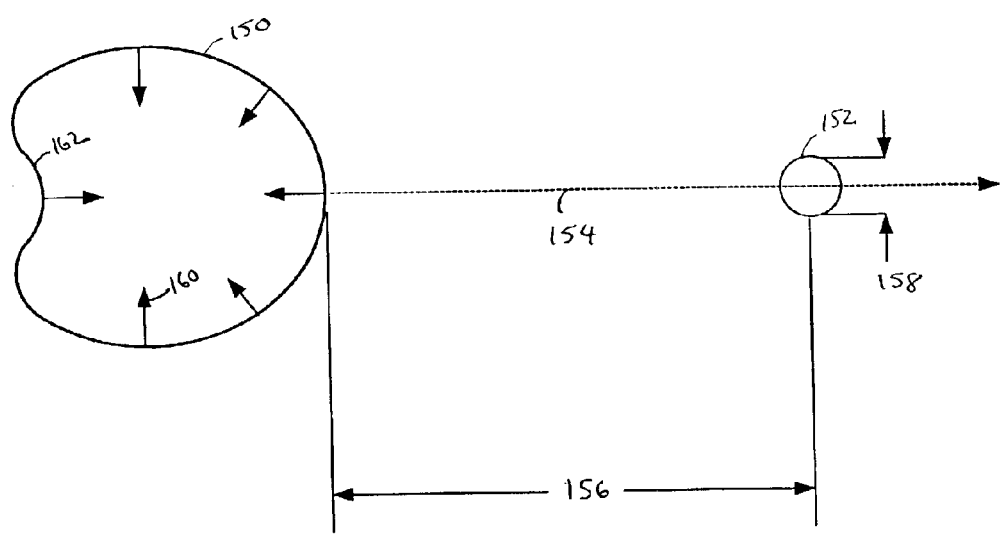
FIG. 2 is a schematic view of a collapsing, working cavitation bubble in relationship to a target bubble in accordance with the present invention.

FIG. 2 is a schematic view of a collapsing, working bubble 150 in relationship to a target bubble 152 in accordance with the present invention. As previously stated, distance 156 should be less than six maximum working bubble diameters. To attract the re-entrant micro-jet formed as bubble 150 collapses, target bubble diameter 158 should be greater than 10% of the maximum working bubble diameter. The projected path of the re-entrant micro-jet is shown by dashed line 154. Inwardly directed arrows 160 in bubble 150 illustrate the beginning collapse of the outer bubble surface. Concave surface 162 is indicative of the direction toward which the jet will be launched. Target bubble 152 may also be a cavitation bubble in an expanding or contracting state, as long as its diameter meets the minimum criteria stated above as working bubble 150 begins to collapse.

FIGS. 3a–3e are schematic diagrams showing a sequence wherein a re-entrant micro-jet is directed toward a work surface through a target bubble in close proximity to the working bubble in accordance with the present invention.

FIG. 3a shows a target cavitation bubble 202 being formed in close proximity to a working cavitation bubble 200. Both bubbles are initiated at approximately the same time, the arrows emanating from the bubble surface and pointing outward illustrate an expanding condition for each bubble. The target bubble 202 is placed between the working bubble 200 and a work piece 204. In this example, the target bubble 202 is within six maximum target bubble diameters of the working bubble 200, and is greater than six maximum target bubble diameters of the work surface. The working bubble 200 is greater than six maximum working bubble diameters, but less than 12 maximum working bubble diameters from the work piece 204. As illustrated, the target bubble 202 is smaller in diameter than the working bubble 200.

FIG. 3b shows at 206 and 208 the working bubble 200 and target bubble 202 at their maximum expanded diameters, just before they collapse.

FIG. 3c shows at 210 and 212 both bubbles 200 and 202 beginning to collapse, as illustrated by the inwardly directed arrows on their outer surface.

FIG. 3d shows the initial formation of the re-entrant micro-jets 216 and 218 by each of the bubbles 200 and 202, respectively. Due to their close proximity, opposing jets are launched from each bubble toward each other.

Figure 3E:
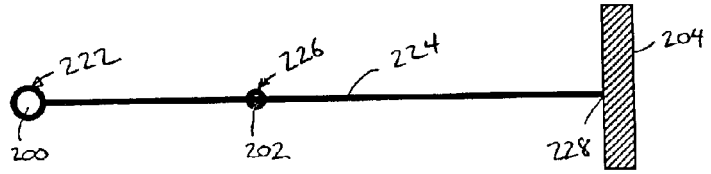

FIG. 3e shows the net effect of the re-entrant micro-jet 224 launched from working bubble 200 through the target bubble 202 to the work surface 228. Since the working bubble 200, as depicted at position 222, was initiated as a larger bubble in comparison to the target bubble, the re-entrant micro-jet launched from it is dominant, resulting in a jet 224 directed toward the work surface. However, the impact force imparted by jet 224 is reduced by the opposing interaction of jet 218 (launched from the target bubble 202) on the initial jet 216 launched by bubble 200. This phenomena may be utilized to moderate and control the impact force imparted by jet 224 on the work surface 204. The closer bubbles 200 and 202 are in maximum diameter (and assuming they are initiated simultaneously), the lower the net force delivered to the work piece 204.

FIGS. 4a–4e are schematic diagrams showing a sequence wherein a re-entrant micro-jet is directed toward a work surface through a target bubble positioned more than six maximum target bubble diameters from the working bubble in accordance with the present invention.

FIG. 4a shows a target cavitation bubble 202 formed in proximity to a working cavitation bubble 200. Both bubbles are initiated at approximately the same time, the arrows emanating from the surface pointing outward illustrate an expanding condition for each bubble. The target bubble 202 is placed between the working bubble 200 and the work piece 204. The working bubble 200 is greater than six maximum working bubble diameters, but less than 12 maximum working bubble diameters from the work piece 204. In this example, the target bubble 202 is within six maximum working bubble diameters of the working bubble 200, but is greater than six maximum target bubble diameters from the working bubble 200 and the work piece 204. As illustrated, the target bubble 202 is smaller in diameter than the working bubble 200.

FIG. 4b shows the working bubble 200 and target bubble 202 at their maximum expanded diameters, just before they collapse.

FIG. 4c shows, at 210 and 230, both bubbles beginning to collapse, as illustrated by the inwardly directed arrows on their outer surface.

FIG. 4d shows the initial formation of the re-entrant micro-jet 216 by bubble 200. Since target bubble 202 is further than six target bubble diameters from bubble 200, it does not "sense" (fluid mechanically) the presence of working bubble 200 and therefore will not launch a jet in its direction. However, target bubble 202 is within six maximum working bubble diameters of bubble 200, and attracts the re-entrant micro-jet from the collapsing working bubble.

Figure 4E:
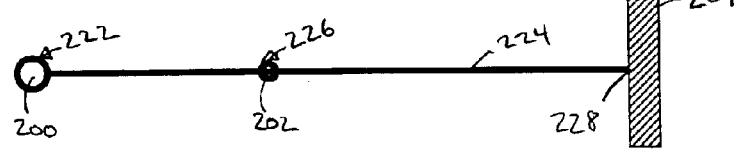

FIG. 4e shows the net effect of the re-entrant micro-jet 224 launched through the target bubble 202 to the work surface 228. In this case the full force of the re-entrant micro-jet formed upon the collapse of the working cavitation bubble is applied to the work surface 228.

FIGS. 5a–5e are schematic diagrams showing a sequence wherein a re-entrant micro-jet is directed toward a work surface at an angle other than 90°, in accordance with the present invention.

Figure 5A:
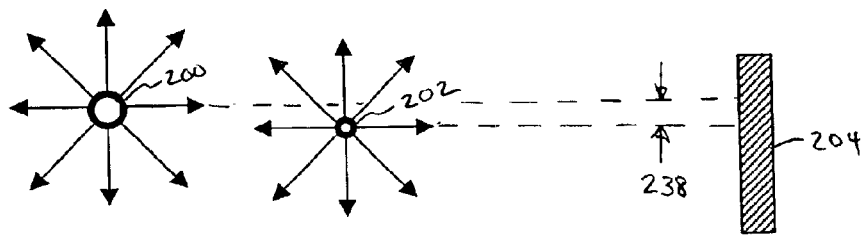
FIGS. 5a–5e are schematic diagrams showing a sequence for directing a re-entrant micro-jet toward a work surface at an angle in accordance with the present invention.

FIG. 5a shows a target cavitation bubble 202 formed in proximity to a working cavitation bubble 200. Both bubbles are initiated at approximately the same time, the arrows emanating from the surface and pointing outward illustrate an expanding condition for each bubble. In this example the target bubble 202 is placed between the working bubble 200 and the work piece 204, but beneath a line normal to the surface of work piece 204 and passing through the center of bubble 200. As so located, target bubble 202 is situated to direct the re-entrant micro-jet from the working bubble 200 at an angle to the surface of 204 as further illustrated below. The working bubble 200 is positioned greater than six maximum working bubble diameters, but less than 12 maximum working bubble diameters from the work piece 204. In this example, the target bubble 202 is within six maximum working bubble diameters of the working bubble 200, but is greater than six target bubble diameters from the working bubble 200. As illustrated, the target bubble 202 is smaller in diameter than the working bubble 200.

Figure 5B:
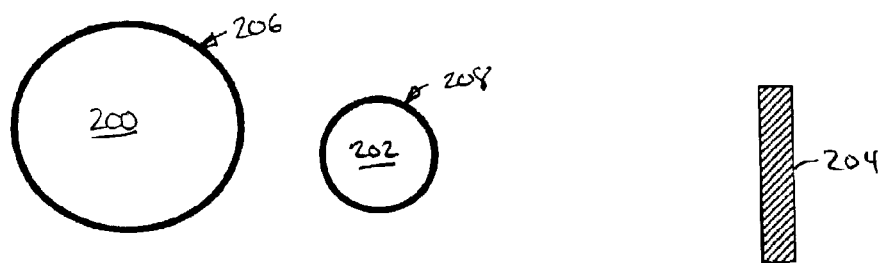

FIG. 5b shows, at 206 and 208 the working bubble 200 and target bubble 202 at their maximum expanded diameters, just before they collapse.

Figure 5C:
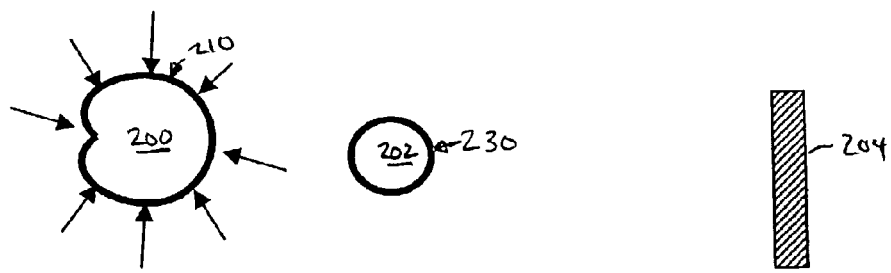

FIG. 5c shows, at 210 and 230, both bubbles 200 and 202 beginning to collapse.

Figure 5D:
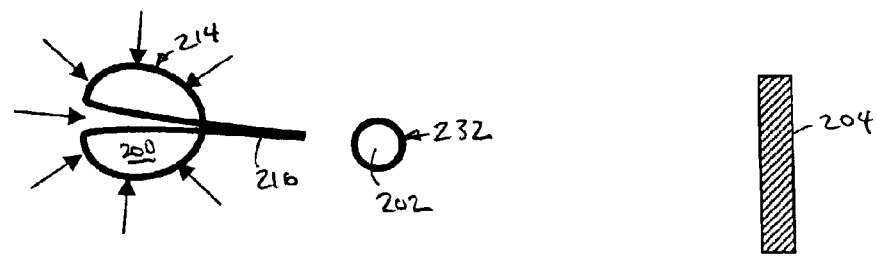

FIG. 5d shows the initial formation of the re-entrant micro-jet 216 by bubble 200. Since collapsing target bubble 202 shown at 232 is further than six maximum target bubble diameters from bubble 200, it does not "sense" (fluid mechanically) the presence of working bubble 200 and therefore will not launch a jet in its direction. Target bubble 202 is within six maximum working bubble diameters of bubble 200 and thus, attracts the re-entrant micro-jet 216 from collapsing working bubble 200.

Figure 5E:
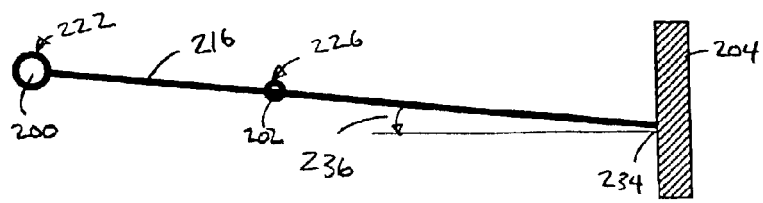

FIG. 5e shows the net effect of the re-entrant micro-jet 224 launched through the target bubble 202 to the work surface 234. The full force of the re-entrant micro-jet formed upon the collapse of the working cavitation bubble is applied to the work surface 234, at an angle 236. In this manner the target bubble may be used to direct the jet at any selected angle relative to the work surface.

FIGS. 6a–6e are schematic diagrams showing a sequence wherein a re-entrant micro-jet is directed toward a work surface at an angle, where the working bubble and target bubble are both in close proximity to the working surface.

Figure 6A:
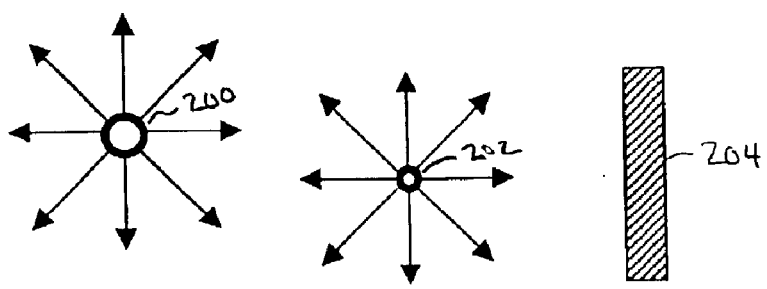
FIGS. 6a–6e are schematic diagrams showing a sequence for directing a re-entrant micro-jet toward a work surface at an angle, for working bubbles and target bubbles in close proximity to the working surface in accordance with the present invention.

FIG. 6a shows a target cavitation bubble 202 formed in proximity to a working cavitation bubble 200. Both bubbles are initiated at approximately the same time, the arrows emanating from the surface pointing outward illustrate an expanding condition for each bubble. The target bubble 202 is placed between the working bubble 200 and the work piece 204, and again beneath a normal line passing through bubble 200. As in the above case the target bubble 202 is situated to direct the re-entrant micro-jet from the working bubble 200 at an angle to the surface of 204 but not through the target bubble. The working bubble 200 is less than six maximum working bubble diameters from the work piece 204. In this example, the target bubble 202 is also within six maximum working bubble diameters of the working bubble 200, but is greater than six maximum target bubble diameters from the working bubble 200. As illustrated, the target bubble 202 is smaller in diameter than the working bubble 200.

Figure 6B:
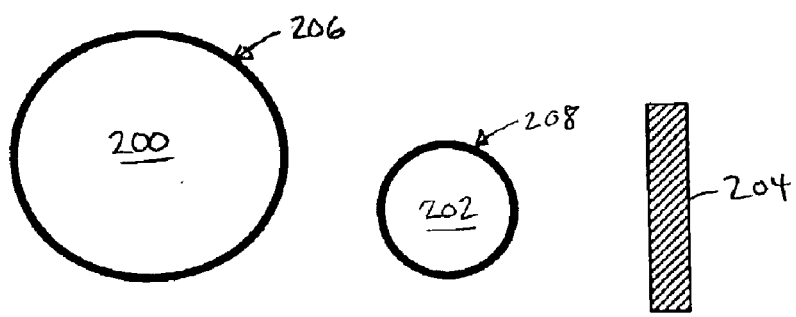

FIG. 6b shows at 206 and 208 the working bubble 200 and target bubble 202 at their maximum expanded diameters, just before they collapse.

Figure 6C:
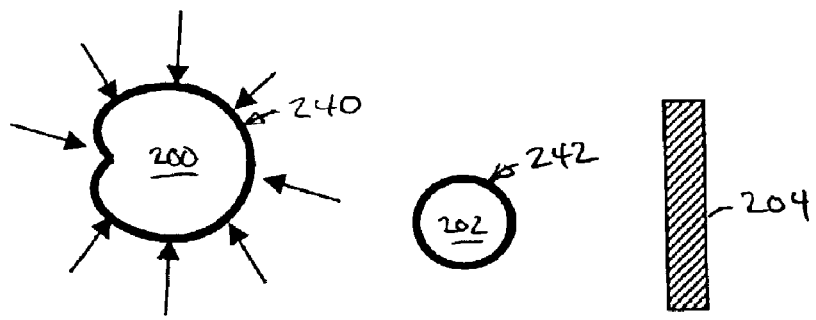

FIG. 6c shows at 240 and 242 both bubbles beginning to collapse.

Figure 6D:
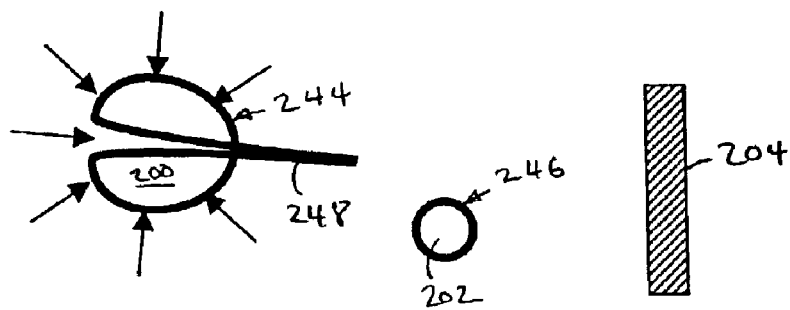

FIG. 6d shows at 244 the initial formation of the re-entrant micro-jet 248 by bubble 200. Since target bubble 202 is further than six maximum target bubble diameters from bubble 200, it does not "sense" (fluid mechanically) the presence of bubble 200 and therefore will not launch a jet in its direction. Since both the target bubble 202 and the work piece 204 are within six maximum working bubble diameters of bubble 200, the re-entrant micro-jet from collapsing working bubble 200 will be launched in a direction between a path normal to the work surface and a path through target bubble 202. Thus, a target bubble having this relationship to working bubble and working surface will tend to direct the micro-jet even through it is not pierced thereby. In the absence of any target bubble, the re-entrant micro-jet would be launched in a direction normal to the surface, but the location of impact would be unpredictable. The target bubble allows fine tuning of the impact location of the re-entrant micro-jet.

Figure 6E:
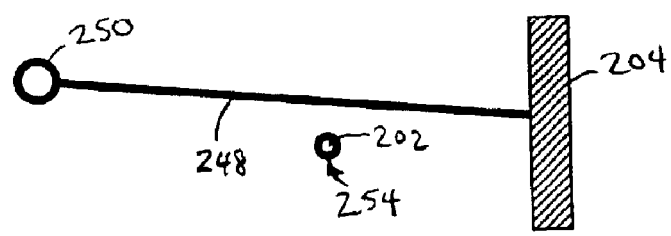

FIG. 6e shows the net effect of the re-entrant micro-jet 248 passing near the target bubble 202 (but not through it) as it projects toward the work piece 204.

FIG. 7 is a schematic diagram of a working bubble 300 and a target bubble 304 directing convergent re-entrant micro-jets 302, 308 to a work surface 314 in accordance with the present invention. In this case, distance 312 is less than six maximum working bubble diameters and distance 310 is less than six target bubble diameters. However, the distance between bubbles 300 and 304 is less than approximately six working bubble diameters but greater than approximately six bubbles diameter. For target bubbles 304 significantly smaller than working bubbles 300, the re-entrant micro-jets emanating from the target bubble will be directed toward the surface 314. As illustrated in the Fig., it is possible to adjust the spatial position of working bubble 300 in order to direct its re-entrant micro-jet 302 to a position convergent with jet 308 from the target bubble 304, as was shown in FIG. 6a–e. This technique may be useful for amplifying the impact of the jets upon the work surface, or providing jets from two different angles to the same location on the work surface.

Figure 8:
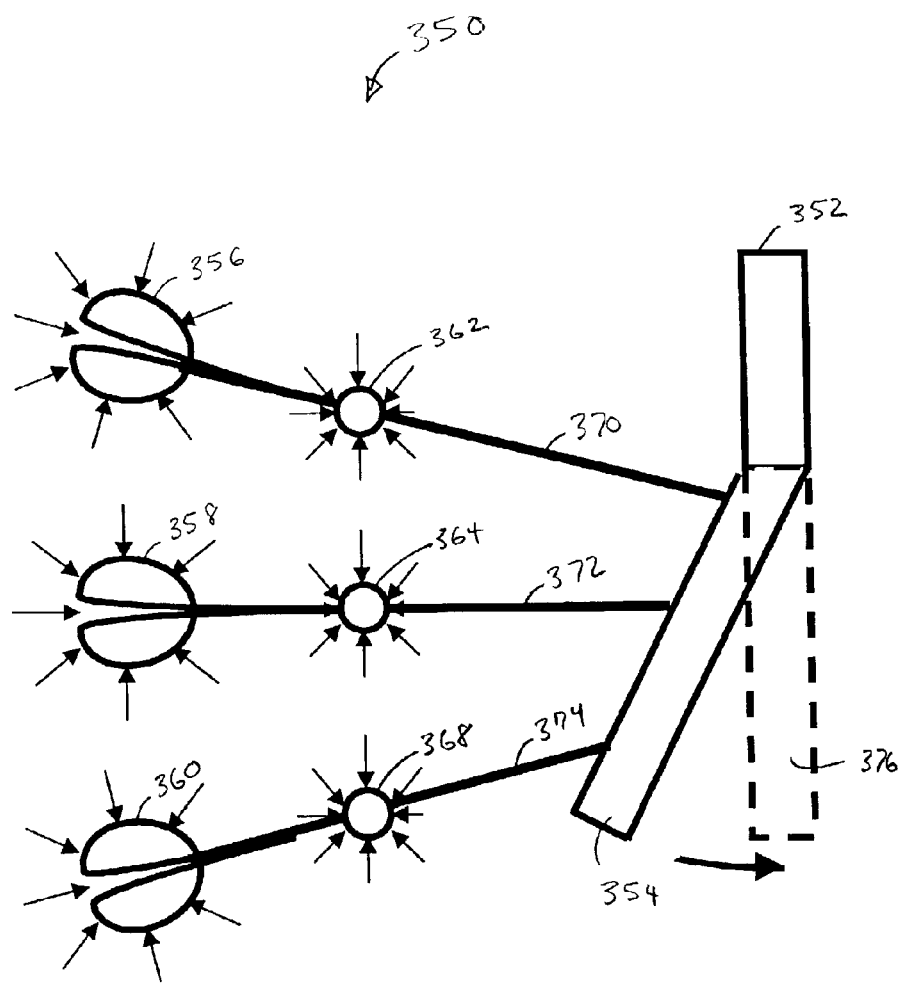
FIG. 8 is a schematic diagram of three re-entrant micro-jets being directed at a movable work piece in accordance with the present invention.

FIG. 8 shows at 350 a schematic diagram 350 of three re-entrant micro-jets being directed at a movable work piece in accordance with the present invention. The three re-entrant micro-jets 370, 372, and 374 are directed at a movable section 354 of work piece 352. Jet 370 is formed by the collapse of cavitation bubble 356 through target bubble 362. Jet 372 is formed by the collapse of cavitation bubble 358 through target bubble 364. Jet 374 is formed by the collapse of cavitation bubble 360 through target bubble 368. Cavitation bubbles 356, 358, and 360 may be formed simultaneously or in a sequence, depending on the sequence of forces required to relocate movable member 354 to its desired location 376. This process may be applied, for example, by a surgeon who wants to precisely locate a small section of tissue that has become detached from its desired position. A folded retina is one such possibility. By adjusting the distance of bubbles 356, 358, and 360 to work piece 354, and their maximum diameters, the forces imparted to tissue may be carefully adjusted to a level sufficient to do the job without imparting collateral damage to the structures being moved.

Figure 9:
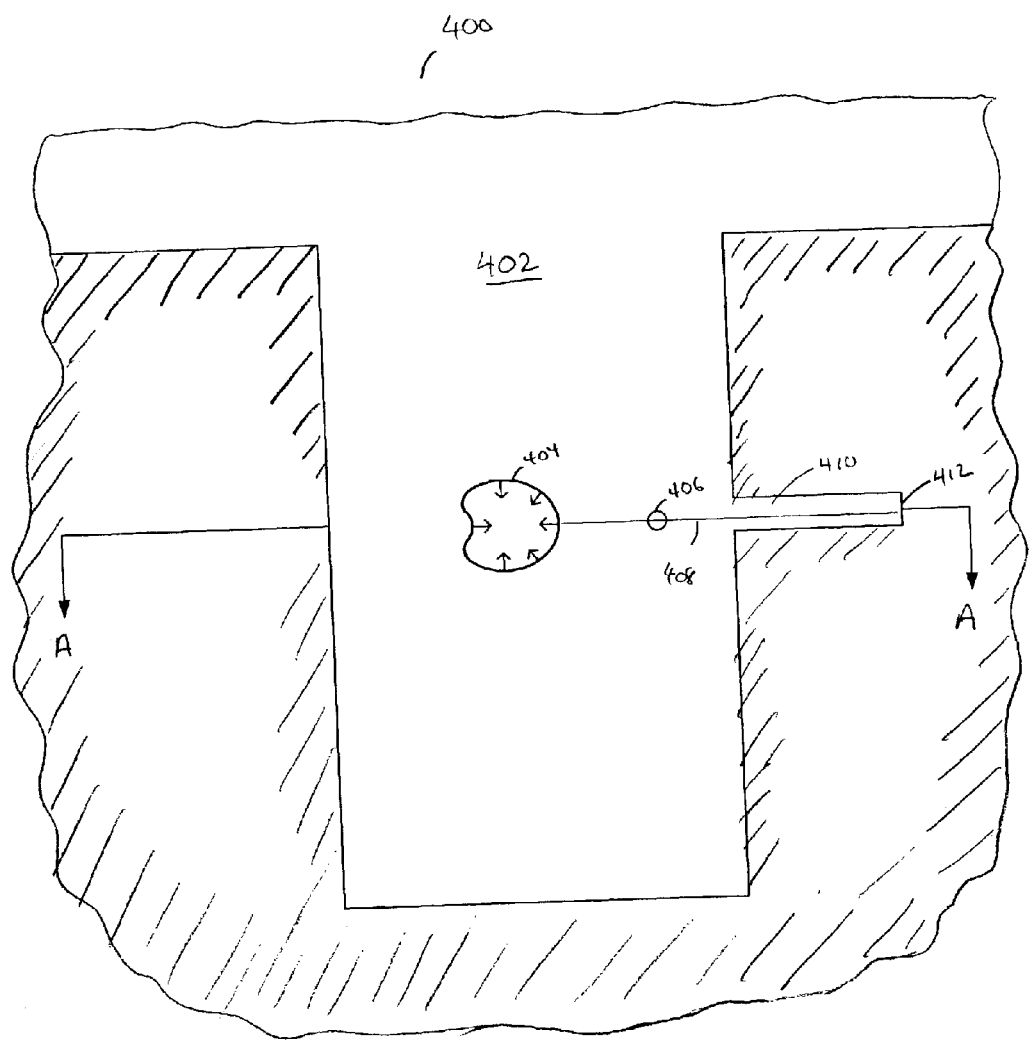
FIG. 9 is a cross sectional view of a cylindrical pore in which the re-entrant micro-jet from a working bubble directed through a target bubble is cutting a cavity in the side wall of the pore in accordance with the present invention.

FIG. 9 is a cross sectional view 400 of a cylindrical pore 420 in which a re-entrant micro-jet 408 from a working cavitation bubble 404 directed through a target bubble 406 is cutting a cavity 410 in the side wall of the pore 402 in accordance with the present invention. Cavitation bubble 404 and target bubble 406 are nucleated within cylindrical pore 402 by any of the methods suggested above. Re-entrant micro-jet 408 directed toward the wall of pore 402 cuts a channel 410 while impinging on surface 412. The depth of channel 410 will depend on the number of times bubbles 404 and 406 are generated. For pore diameters of 5 to 10 microns, re-entrant micro-jets on the order of 10 to 20 nanometers can be created, creating channels in the side walls in the 20 to 30 nanometer range. In silicon substrates, this could allow fabrication of trench capacitor structures of extremely small dimension, utilizing a volume of the substrate not accessible previously. The fabrication technology may enable true three dimensional device fabrication strategies to produce nanometer device geometry's without the use of lithography.

Figure 10:
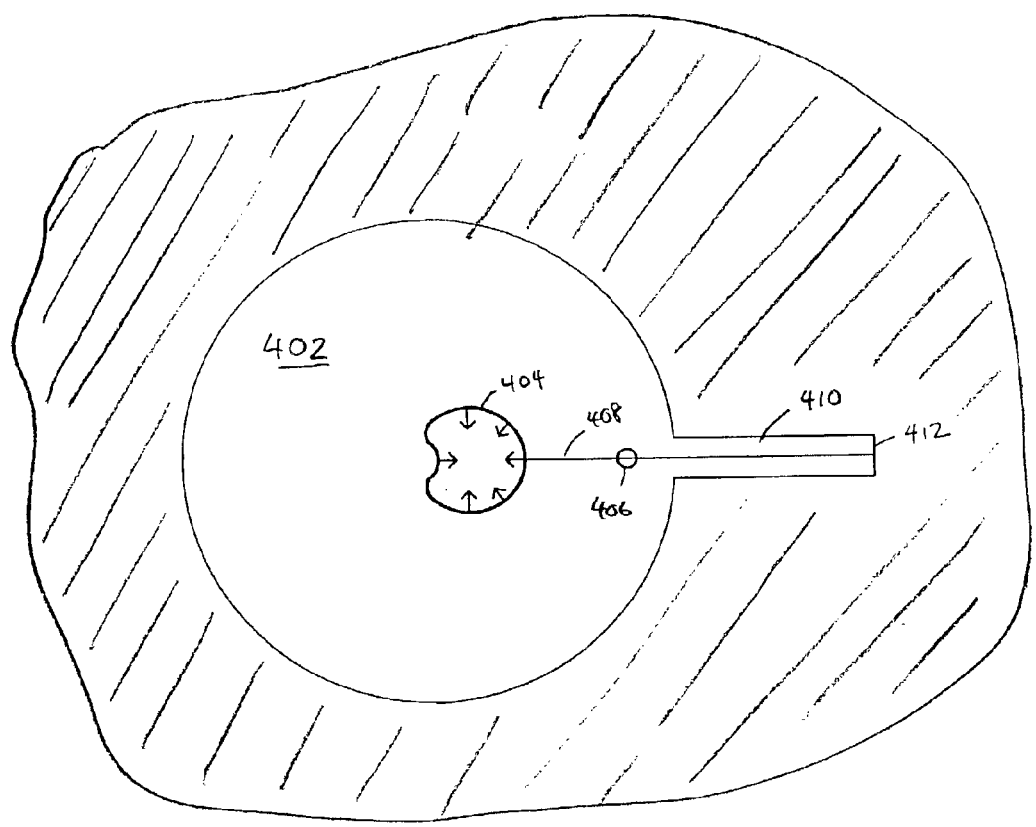
FIG. 10 is a cross sectional view taken along the line A—A of FIG. 9.

FIG. 10 is a cross-sectional view taken along the line A—A in FIG. 9 looking into the cylindrical pore 402.

Figure 11:
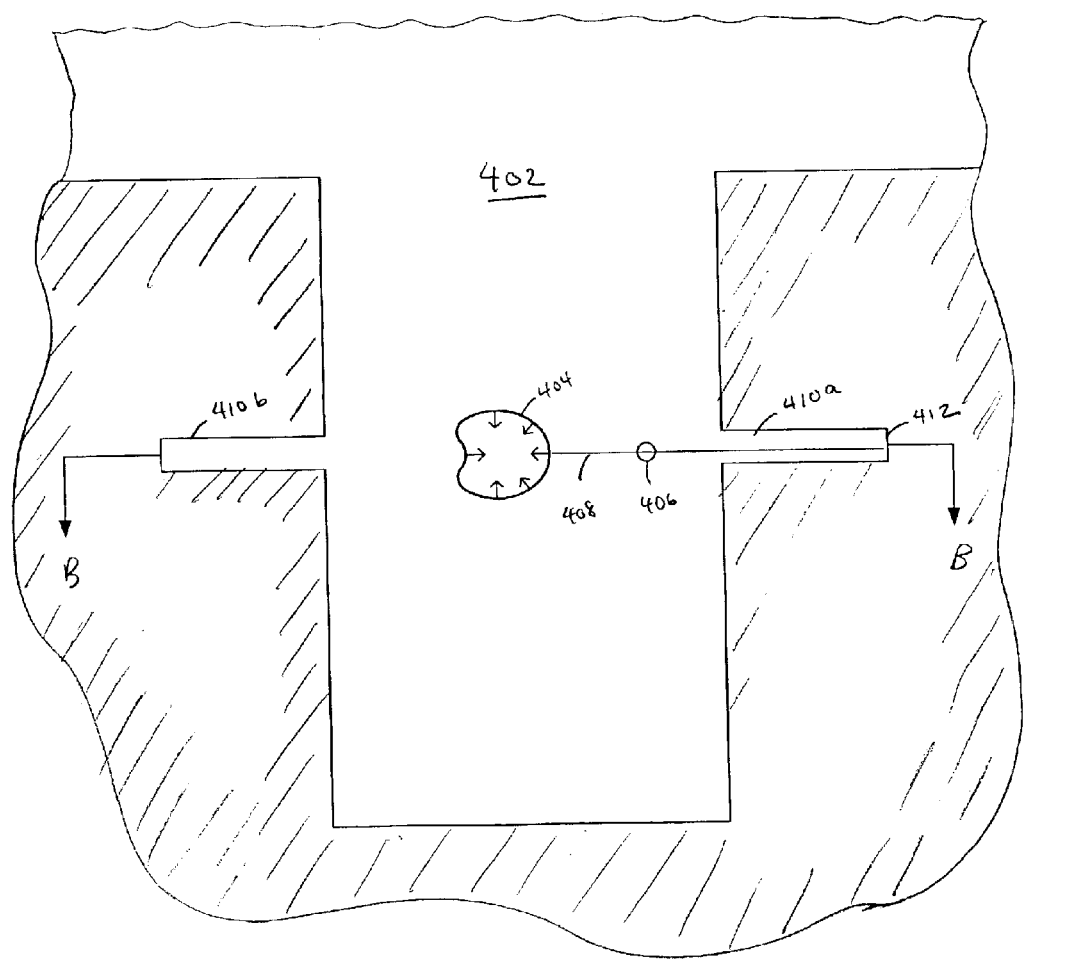
FIG. 11 is a cross sectional view of a cylindrical pore where the re-entrant micro-jets from working bubbles directed through target bubbles have cut multiple cavities in accordance with of the present invention.

FIG. 11 is a cross sectional view of a cylindrical pore where re-entrant micro-jets from working bubbles directed through target bubbles are cutting multiple cavities in accordance with the present invention. As in this example of FIGS. 9 and 10, cavitation bubbles 404 can be used with target bubbles 406 to cut multiple cavities 410a and 410b. This can be accomplished by placing target bubble 406 in the appropriate position relative to working bubbles 404.

Figure 12:
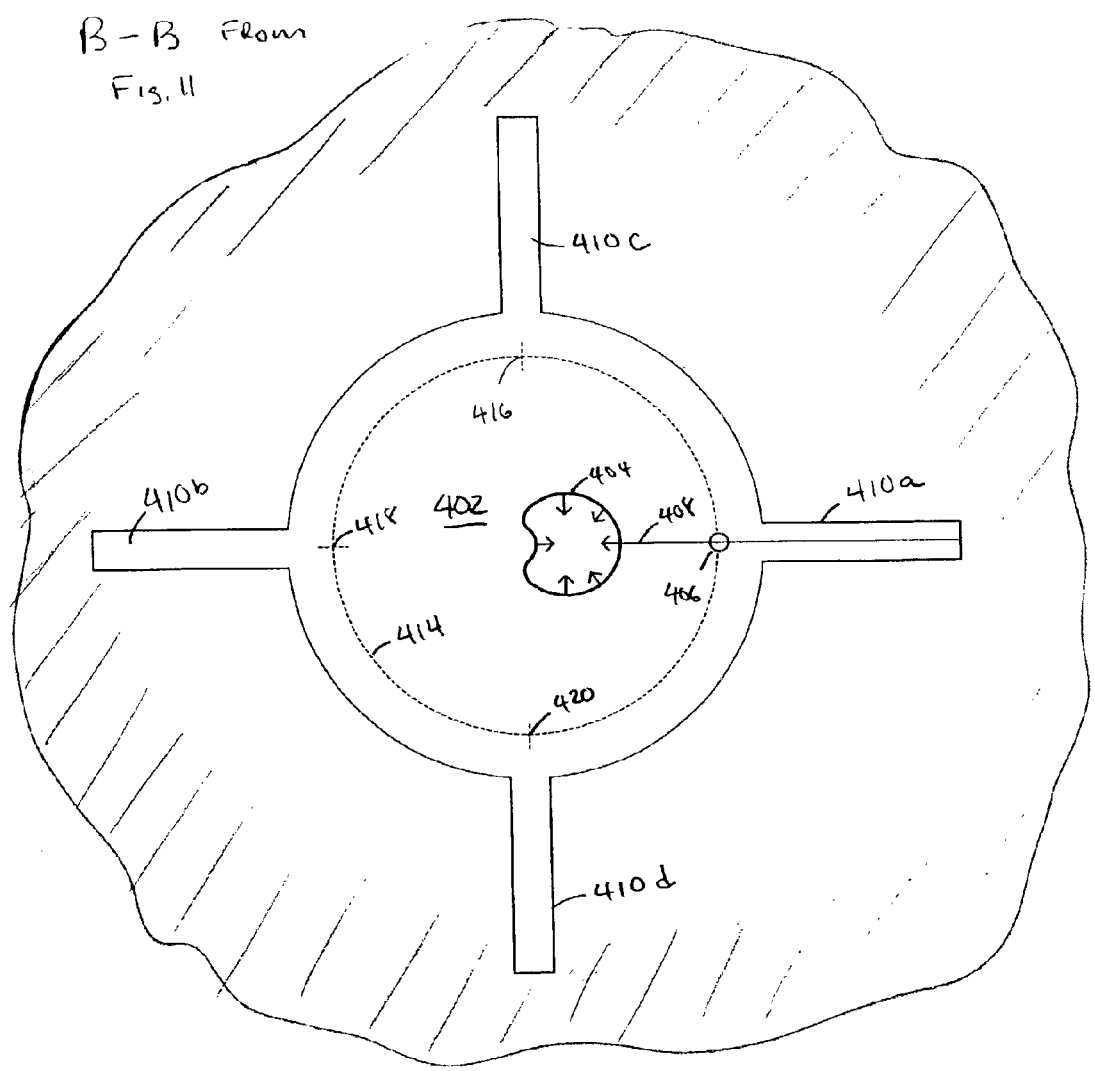
FIG. 12 is a cross sectional view taken along line B—B of FIG. 11.

FIG. 12 is a cross-sectional view taken along the line B—B in FIG. 11 and, looking into the pore of FIG. 11 showing multiple cavities formed at 90 degree angles relative to the pore axis. By positioning the target bubble 406 on dotted circular path 414 at positions 418, 416, and 420, cavities 410b, 410c, and 410d can be fabricated, respectively. Although four cavities are shown in this figure, many others at any desired spacing can be fabricated as will be appreciated by those skilled in the art.

Figure 13:
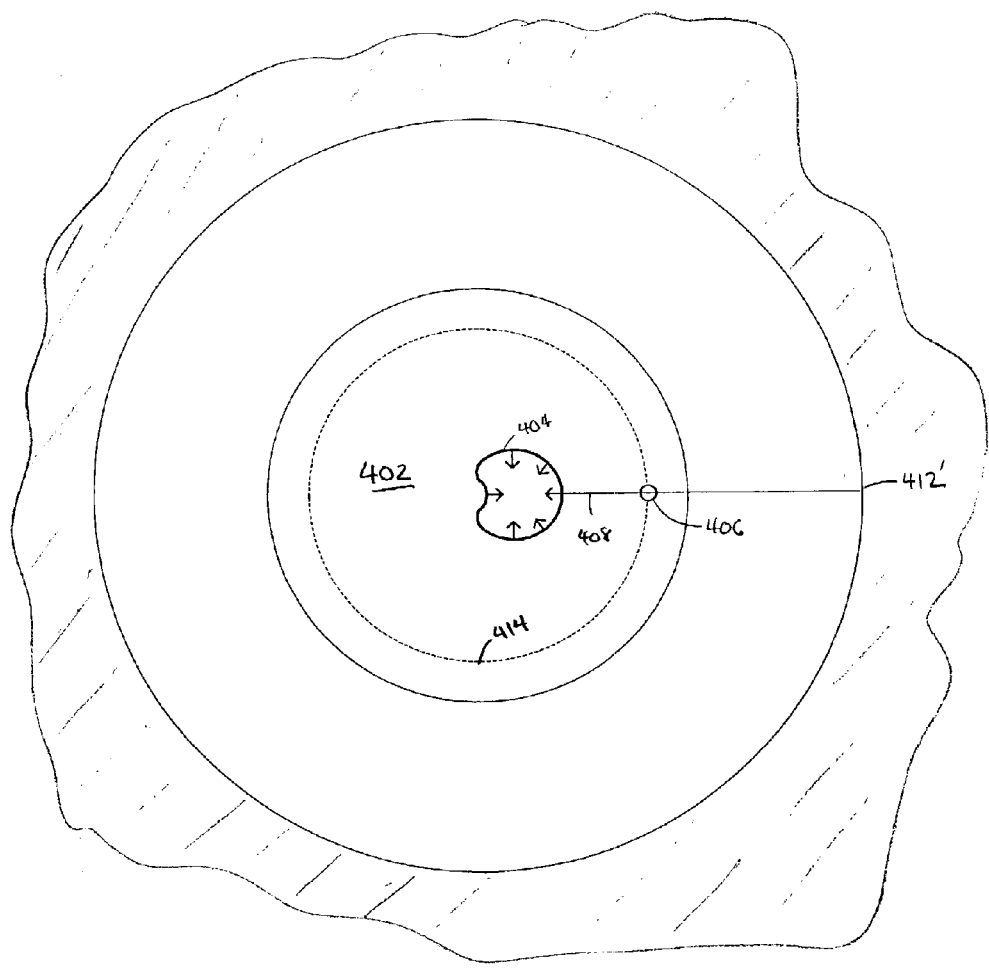
FIG. 13 is a cross sectional view similar to that of FIG. 12 except that the re-entrant micro-jets have cut an annular ring around a cylindrical pore.

FIG. 13 is a cross sectional view similar to that of FIG. 12, except that instead of using the working and target bubbles to drill dicrete cavities, they are used to form a continuous horizontal slot in the wall of the pore 402. More specifically, when a series of cavitation target bubbles 406 are moved in a continues manner along path 414, and properly timed with the generation of working bubbles 404, a resulting horizontal slot at depth 412' can be produced. By altering the depth (along the axis of pore 402) that working bubble 404 and target bubble 406 are situated in the pore 402, multiple horizontal slots at varying depths can be fabricated as well. Due to the intense power of the re-entrant micro-jets, the hardest materials can be eroded with this technique, including crystalline silicon. Multiple slots produced in a horizontal fashion could provide a basis for very high surface area capacitors for advanced memory devices, for example.

Figure 14:
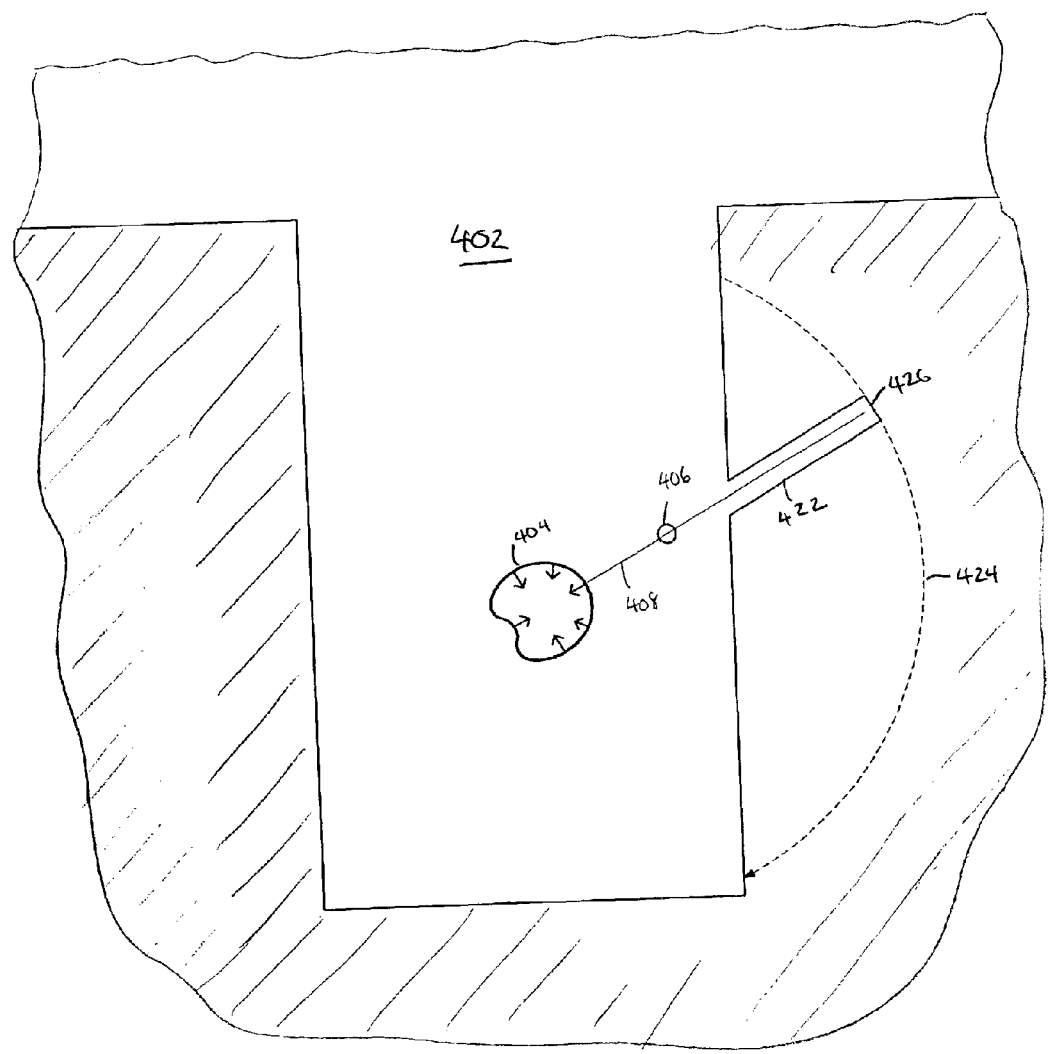
FIG. 14 is a cross sectional view of a cylindrical pore wherein the re-entrant micro-jets from working bubbles directed through target bubbles have cut a cavity at an angle other than normal to the surface of the pore in accordance with the present invention.

FIG. 14 is a cross sectional view of a cylindrical pore 402 wherein re-entrant micro-jets 408 from working bubbles 404 directed through target bubbles 406 are cutting a cavity at an angle not normal to the surface of the pore in accordance with the present invention. In this case target bubble 406 is placed in a horizontal plane above or below cavitation bubble 404. If the position of bubbles 404 and 406 are held constant, the re-entrant micro-jet 408 will cut a cavity 422 at an angle to the vertical wall of pore 402. By placing target bubble 406 at different fixed depth intervals, cavities at various angles of depth 426 can be produced. Similarly, by adjusting the depth of target bubble 406 in a continuos manner, a larger cutout following the outline 424 may be obtained. By applying the techniques illustrated in the previous FIGS. 9–14, practically any profile or shape can be fabricated in the walls of a pore.

Figure 15:
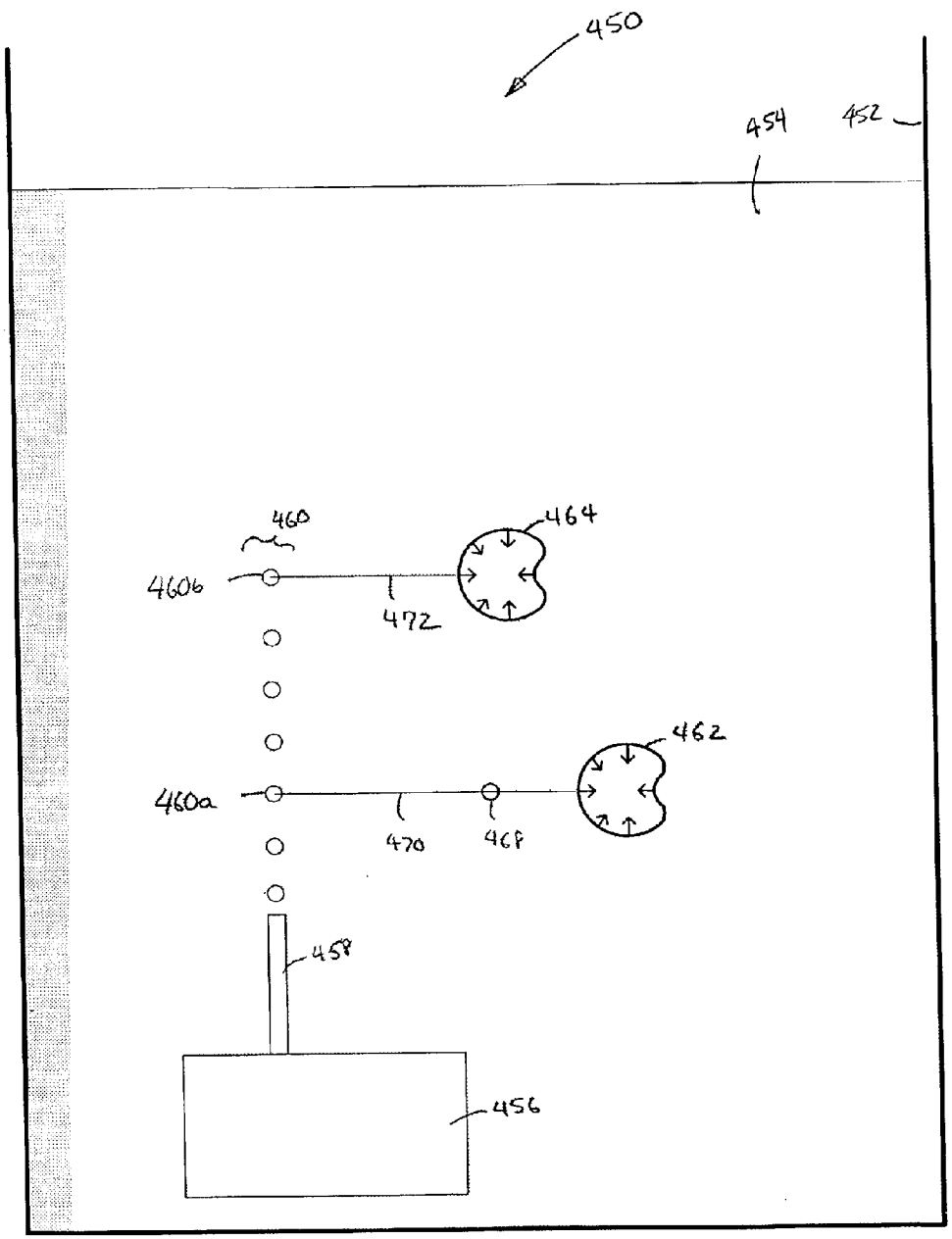
FIG. 15 is a schematic view of an alternative embodiment of the present invention illustrating a cavitation based process for injecting solution components into liposomes.

FIG. 15 is a schematic view of a cavitation based process for injecting solution components into liposomes in accordance with an alternative embodiment of the present invention. Liposomes are microscopic, fluid-filled pouches whose walls are made of layers of phospholipids identical to the phospholipids that make up cell membranes. The fluid inside the pouch may contain soluble drugs designed to be delivered to cells when the liposomes merge with the cell walls of a targeted cell. One way to inject the drug into the interior of a liposome is shown at 450 in this figure. As depicted, container 452 contains a fluid solution 454, a liposome manufacturing module 456 (which can also reside outside the walls of container 452), and a nozzle 458 for delivering liposomes 460 into the fluid 454. The liposomes may be manufactured with no drugs in their interiors, some amount of the desired drug, or a mixture of completely different drugs. The drugs to be injected are present in the solution 454. In one example, a cavitation bubble 464 is nucleated within five bubble diameters of a liposome 460b. The liposome acts like a target bubble, attracting the re-entrant micro-jet 472. Adjustment of the control volume and initial energy dose will determine the size of the cavitation bubble, and therefore the size of micro-jet 472. The collapsing cavitation bubble entrains components of the solution 454, including the drugs to be injected, and the micro-jet 472 delivers these components through the wall of the liposome 460b. In a second example, a target bubble 468 is nucleated in proximity to a working bubble 462, in such a manner as to direct a re-entrant micro-jet 470 into the interior of liposome 460a. This method allows the working bubble 462 to be a further distance from liposome 460a, allowing additional flexibility in reducing dosage levels injected into the liposome, as well as reducing the potentially damaging impact of a jet launched in close proximity.

What is claimed is:

1. An apparatus for the directed formation of a re-entrant micro-jet comprising:
  a vessel containing a liquid within which a work piece having a work surface may be immersed;
  a first energy source for producing a first energy flow in said liquid sufficient to create a working cavitation bubble proximate to said work surface; and
  a second energy source for producing a second energy flow in said liquid sufficient to create a target cavitation bubble between said work surface and said working cavitation bubble, wherein a first re-entrant micro-jet formed upon the collapse of said working cavitation bubble, the direction of which engages said work surface, is influenced by the position of said target bubble.

2. An apparatus as recited in claim 1, wherein,
  said working cavitation bubble expands to attain a predetermined working bubble diameter;
  said target bubble is within a distance of six said predetermined working bubble diameters of the center of said working cavitation bubble.

3. The apparatus of claim 2, wherein, the diameter of said target bubble is greater than 10% of said predetermined working bubble diameter prior to the collapse of said working cavitation bubble.

4. An apparatus as recited in claim 2, wherein,
  said target bubble attains a predetermined target bubble diameter during expansion; and
  said target bubble is positioned a distance greater than six said predetermined target bubble diameters from a surface of said working bubble.

5. An apparatus as recited in claim 1, wherein, the relative positions of said working bubble, said target bubble, and said work surface are such that said first re-entrant micro-jet is directed through said target bubble to said work surface.

6. An apparatus as recited in claim 1, wherein, said first energy source is a laser.

7. An apparatus as recited in claim 6, wherein, said laser is selected from the group consisting of an excimer laser, a dye laser, a Nd-YAG laser, and a CO2 laser.

8. An apparatus as recited in claim 1, wherein, said first energy source is an x-ray source.

9. An apparatus as recited in claim 1, wherein, said first energy source is an electrical discharge device.

10. An apparatus as recited in claim 1, wherein, said second energy source is a laser.

11. An apparatus as recited in claim 10, wherein, said laser is selected from the group consisting of an excimer laser, a dye laser, a Nd-YAG laser, and a CO2 laser.

12. An apparatus as recited in claim 1, wherein, said second energy source is an x-ray source.

13. A method for the directed formation of a re-entrant micro-jet comprising:
  immersing a work piece having a work surface in a liquid;
  generating a working cavitation bubble proximate to said work surface; and
  generating a target bubble between said work surface and said working cavitation bubble, said target bubble influencing the direction at which a first re-entrant micro-jet formed upon the collapse of said working cavitation bubble engages said work surface.

14. A method as recited in claim 13, wherein,
  said working cavitation bubble attains a predetermined working bubble diameter during expansion;
  said target bubble is within a distance of six said predetermined working bubble diameters of the center of said working cavitation bubble.

15. A method as recited in claim 14, wherein, the diameter of said target bubble is greater than 10% of said predetermined working bubble diameter prior to the collapse of said working cavitation bubble.

16. A method as recited in claim 15, wherein, said target bubble is a cavitation bubble.

17. A method as recited in claim 16, wherein,
  said target bubble attains a predetermined target bubble diameter during expansion; and
  said target bubble is positioned at distance greater than six said predetermined target bubble diameters from a surface of said working bubble.

18. A method as recited in claim 16, wherein,
  said target bubble is located within six of said predetermined target bubble diameters of said work surface;
  said working bubble is located within six of said predetermined working bubble diameters of said work surface; and
  said target bubble launches a second re-entrant micro-jet toward said work surface.

19. A method as recited in claim 15, wherein, said target bubble is a gas bubble.

20. A method as recited in claim 13, wherein, said first re-entrant micro-jet is directed through said target bubble to said work surface.

21. A method as recited in claim 13, wherein, said work piece is a liposome.

* * * * *